(12) United States Patent
Castaneda-Lopez et al.

(10) Patent No.: US 10,082,478 B2
(45) Date of Patent: Sep. 25, 2018

(54) METHODS FOR EVALUATION AND ESTIMATION OF EXTERNAL CORROSION DAMAGE ON BURIED PIPELINES

(71) Applicants: Homero Castaneda-Lopez, Hudson, OH (US); Ayako Yajima, Hudson, OH (US); Ximing Li, Parma, OH (US); Qindan Huang, Stow, OH (US)

(72) Inventors: Homero Castaneda-Lopez, Hudson, OH (US); Ayako Yajima, Hudson, OH (US); Ximing Li, Parma, OH (US); Qindan Huang, Stow, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/304,187

(22) PCT Filed: Apr. 15, 2015

(86) PCT No.: PCT/US2015/025938
§ 371 (c)(1),
(2) Date: Oct. 14, 2016

(87) PCT Pub. No.: WO2015/160927
PCT Pub. Date: Oct. 22, 2015

(65) Prior Publication Data
US 2017/0030850 A1   Feb. 2, 2017

Related U.S. Application Data

(60) Provisional application No. 61/979,738, filed on Apr. 15, 2014.

(51) Int. Cl.
*G01R 27/08* (2006.01)
*G01N 27/12* (2006.01)
(Continued)

(52) U.S. Cl.
CPC .......... *G01N 27/121* (2013.01); *G01N 17/02* (2013.01); *G01N 27/20* (2013.01); *G01N 27/61* (2013.01); *G01N 33/246* (2013.01)

(58) Field of Classification Search
CPC ...... G01N 27/121; G01N 17/02; G01N 27/20; G01N 27/61; G01N 33/246
See application file for complete search history.

(56) References Cited

U.S. PATENT DOCUMENTS

2009/0281746 A1   11/2009   McDonnell et al.

FOREIGN PATENT DOCUMENTS

CN   203465238 U   3/2014

OTHER PUBLICATIONS

Ukiwe et al., Improving the Effectiveness of Indirect Inspection Surveys, NACE International, 2012.*
(Continued)

*Primary Examiner* — Daniel Miller
(74) *Attorney, Agent, or Firm* — Renner Kenner Greive Bobak Taylor & Weber

(57) ABSTRACT

A method to assess external corrosion in buried pipelines includes analysis of moisture content of soil along the length of the pipe to choose the most appropriate indirect inspection methods. External corrosion is assessed based on the unification of probability techniques using clustered inspection data and deterministic formulation for soil conditions. A deterministic model pinpoints the location of the most likely areas for corrosion due to the electrochemical cell formation produced by the presence of water and the properties of the soil, such as ion concentrations, pH, soil resistivity, redox potential, corrosion potential and soil type. The filtering of the data by clustering provides reliable results to locate the most corrosive locations. The failure probability is calculated based on in-line inspection data, where different indi-
(Continued)

cations could appear and different dimensions are used to link the corrosivity with the failure for choosing repairing methods and taking actions against corrosion.

6 Claims, 11 Drawing Sheets

(51) Int. Cl.
*G01N 27/20* (2006.01)
*G01N 27/61* (2006.01)
*G01N 17/02* (2006.01)
*G01N 33/24* (2006.01)

(56) References Cited

OTHER PUBLICATIONS

Indirect Inspection, presented by Jim Walton at Appalachian Underground Corrosion Short Course, 2012, available online at: https://www.aucsc.com/_aucsc%20speaker%20files/Pipeline%20Integrity%20Mgt20Periods%204%20&%205%20Indirect%20Inspection%20Tools%20ACVG%20CA%2020and%20DCVG.pdf.*

Kendy et al., A soil-water-balance approach to quantify groundwater recharge from irrigated cropland in the North China Plain, Hydrol. Process. 17, 2011-2031, 2003.*

Ruschau, G "Field Investigation of Aboveground Techniques for Detecting Coating Anomalies". Corrosion Mar. 12-16, 2006, NACE-06191, San Diego, California, NACE International2006 [retrieved from internet: Jun. 3, 2015) <URL: https://www.onepetro.org/conference-paper/NACE-06191?sort=&start=O&q=FIELD+INVESTIGATION+OF+ABOVEGROUND+TECHNIQUES+FOR+DETECTING+COATING+ANOMALIES&from_year=&peer_reviewed=&published_between=&fromSearchResults=true&to_year=&rows=10#>; p. 1, paragraph 2; p. 3, paragraph 4.

Castaneda, H "Detecting External Failures in Coated Buried Pipelines: Theoretical Model and Experimental Verificaiton", Jun. 2004 [retrieved from internet: Jun. 2, 2015) <URL: https://www.onepetro.org/journal-paper/NACE-04060538>; p. 7, paragraph 4, figures 9 & 11.

* cited by examiner

| Location | Total number of defects | Segment number |
|---|---|---|
| 1 | 121 | 1 |
| 2 | 16 | |
| 3 | 7 | |
| 4 | 6 | |
| 5 | 16 | |
| 6 | 7 | |
| 7 | 28 | |
| 8 | 5 | |
| 9 | 12 | 2 |
| 10 | 4 | |
| 11 | 15 | |
| 12 | 2 | |
| 13 | 4 | |
| 14 | 14 | |
| 15 | 108 | |
| 16 | 7 | |
| 17 | 7 | 3 |
| 18 | 3 | |
| 19 | 2 | |
| 20 | 3 | |
| 21 | 0 | |
| 22 | 2 | |
| 23 | 0 | |
| 24 | 7 | |
| 25 | 2 | 4 |
| 26 | 15 | |
| 27 | 10 | |
| 28 | 5 | |
| 29 | 12 | |
| 30 | 12 | |
| 31 | 12 | |
| 32 | 12 | |
| 33 | 6 | 5 |
| 34 | 0 | |
| 35 | 36 | |
| 36 | 7 | |
| 37 | 2 | |
| 38 | 7 | |
| 39 | 3 | |
| 40 | 4 | |
| 41 | 5 | 6 |
| 42 | 53 | |
| 43 | 23 | |
| 44 | 2 | |
| 45 | 6 | |
| 46 | 21 | |
| 47 | 2 | |
| 48 | 10 | |
| 49 | 12 | 7 |
| 50 | 8 | |
| 51 | 16 | |
| 52 | 5 | |
| 53 | 22 | |
| 54 | 5 | 8 |
| 55 | 6 | |
| 56 | 7 | |
| 57 | 47 | |
| 58 | 0 | NA |
| 59 | 0 | |
| 60 | 8 | |
| 61 | 3 | |
| 62 | 3 | |
| 63 | 80 | |
| 64 | 43 | 9 |
| 65 | 33 | |
| 66 | 8 | 10 |
| 67 | 16 | |
| 68 | 17 | |
| 69 | 19 | |
| 70 | 26 | |
| 71 | 16 | |
| 72 | 14 | |
| 73 | 28 | 11 |
| 74 | 16 | |
| 75 | 4 | |
| 76 | 17 | |
| 77 | 44 | |
| 78 | 20 | |
| 79 | 19 | |
| 80 | 11 | |
| 81 | 8 | 12 |
| 82 | 42 | |
| 83 | 13 | |
| 84 | 2 | |
| 85 | 3 | |
| 86 | 4 | |
| 87 | 0 | |
| 88 | 2 | |
| 89 | 27 | 13 |
| 90 | 76 | |
| 91 | 68 | |
| 92 | 7 | |
| 93 | 32 | |
| 94 | 53 | |
| 95 | 49 | |
| 96 | 39 | |
| 97 | 43 | 14 |
| 98 | 103 | |
| 99 | 74 | |
| 100 | 42 | |
| 101 | 73 | |
| 102 | 159 | |
| 103 | 84 | |
| 104 | 44 | |
| 105 | 55 | 15 |
| 106 | 55 | |
| 107 | 84 | |
| 108 | 105 | |
| 109 | 108 | |
| 110 | 77 | |
| 111 | 118 | |
| 112 | 66 | |

Fig. 7

METHODS FOR EVALUATION AND ESTIMATION OF EXTERNAL CORROSION DAMAGE ON BURIED PIPELINES

CROSS-REFERENCE TO RELATED APPLICATIONS

This application claims priority to U.S. Provisional Patent Application No. 61/979,738, filed Apr. 15, 2014, the entirety of which is incorporated herein by reference.

FIELD OF THE INVENTION

The present invention relates to methods for evaluating external corrosion damage in buried pipelines.

BACKGROUND OF THE INVENTION

The present invention improves upon the known ANSI (American National Standards Institute) and NACE International (National Association of Corrosion Engineers International Institute) Standard Practice Pipeline External Corrosion Direct Assessment Methodology, ANSI/NACE SP0502 (herein ECDA). This standard methodology includes the following steps: pre-assessment, indirect inspection, direct inspection, and post assessment. The present invention additional methodologies within these generally known steps to improve the process and particularly

SUMMARY OF THE INVENTION

In a first embodiment, the present invention provides a method for assessing damage to the exterior of a buried pipeline. The method for assessing damage to the exterior of a buried pipeline comprising the steps of: calculating the moisture content of the soil through which the pipeline extends at a plurality of locations along the length of the pipeline and conducting holidays indirect inspection of the plurality of locations through the application of alternating current voltage gradient surveys and direct current voltage gradient surveys, wherein at locations where the moisture content is low, ACVG is applied and, at locations where the moisture content is high, DCVG is applied.

In a second embodiment, the present invention provides a method for assessing damage to the exterior of a buried pipeline as in the first embodiment, wherein moisture content is calculated according to:

$$\theta_i^r - \theta_s - \frac{\theta_s - \theta_r}{\alpha} \ln\left[\frac{\alpha K_s}{L(\theta_s - \theta_r)} + \exp\left(\alpha \frac{\theta_s - \theta_{start}}{\theta_s - \theta_r}\right)\right].$$

In a third embodiment, the present invention provides a method for assessing damage to the exterior of a buried pipeline as in either the first or second embodiment, wherein, if $\theta_i^t$ is less than or equal to 0.1, ACVG is applied, and, if $\theta_i^t$ is greater than 0.1, DCVG is employed.

In a fourth embodiment, the present invention provides a method for assessing damage to the exterior of a buried pipeline as in any of the first through third embodiments, wherein the method further comprising the step of conducting soil indirect inspection of the plurality of locations to obtain soil properties selected from the group consisting of moisture content, pH, ion concentrations, soil resistivity, redox potential, corrosion potential and soil type, wherein ion concentrations are selected from concentrations of $HCO^{3-}$, $Cl^-$, $SO_4^{2+}$ and $CO_3^{2-}$.

In a fifth embodiment, the present invention provides a method for assessing damage to the exterior of a buried pipeline as in any of the first through fourth embodiments, wherein the method further comprising the steps of conducting pigging inspection of the plurality of locations and thereby identifying defects within the wall of the pipeline and providing data regarding the metal loss at each defect and calculating metal loss rates from the data regarding the metal loss at each defect.

In a sixth embodiment, the present invention provides a method for assessing damage to the exterior of a buried pipeline as in any of the first through fifth embodiments, wherein the method further comprising the step of clustering the data regarding metal loss rates with the moisture content calculated in the step of calculating the moisture content and with the soil properties of the step of conducting soil indirect inspection.

BRIEF DESCRIPTION OF THE DRAWINGS

FIG. 3 shows a type of in-line inspection, wherein well known inspection devices—known as "pigs" and carrying out a process known as "pigging"—travel the desired length of the pipe and collect data regarding the corrosion of the pipe and/or other desired data, such as soil conditions or water content and the like;

FIG. 7 is a chart showing how a 112 km length of the pipeline is grouped into segments to assess defects, with defects being shown per mile-long segment;

DETAILED DESCRIPTION OF ILLUSTRATIVE EMBODIMENTS

Figure 1:
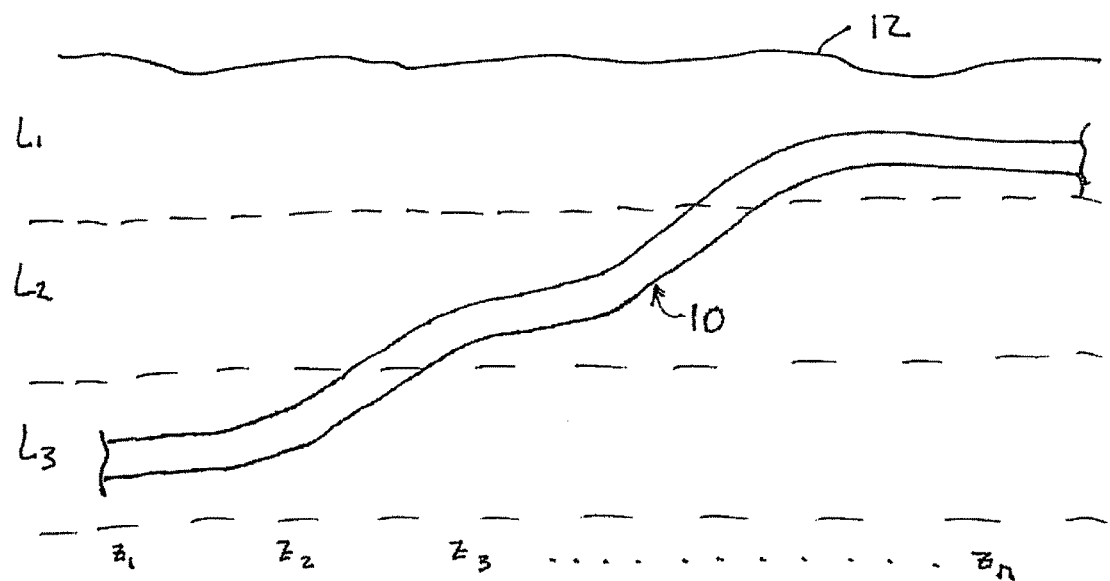
FIG. 1 is a schematic representation of a length of pipe extending through multiple layers of soil, and is used to help describe the method herein, which involves analysis of the pipe at various points and along various segments.

A method is provided to assess external corrosion in buried pipelines. Analysis of moisture content of soil along the length of the pipe helps to choose the most appropriate indirect inspection methods, and, after this indirect inspection, external corrosion is assessed based on the unification of probability techniques using clustered inspection data and deterministic formulation for soil conditions. The method employs a deterministic model that pinpoints the location of the most likely areas for corrosion due to the electrochemical cell formation produced by the presence of water and the properties of the soil, such as ion concentrations, pH, soil resistivity, redox potential, corrosion potential and soil type. Ion concentrations of particularly interest include the concentrations of ions selected from $HCO^{3-}$, $Cl^-$, $SO_4^{2+}$ and $CO_3^{2-}$. The method also provides a stochastic model combined with clustering algorithms that can ascertain the similarity of corrosion defects. Monte Carlo simulation can be employed to provide an accurate probability density function estimation of the corrosion rate. The filtering of the data by clustering provides reliable results to locate the most corrosive locations. The failure probability is calculated based on the in line inspection data, where different indications could appear and different dimensions are used to link the corrosivity with the failure for the repairing methods and control actions against corrosion.

The method improves upon aspects of the ANSI (American National Standards Institute) and NACE Standard Practice Pipeline External Corrosion Direct Assessment Methodology, ANSI/NACE SP0502 (herein ECDA). This standard methodology includes the following steps: pre-assessment, indirect inspection, direct inspection, and post assessment. Notably, while ECDA as described in the ANSI/NACE standard practice is specifically intended to address buried onshore pipelines constructed from ferrous materials, the concepts of the present invention can be used to assess external corrosion in buried pipelines of non-ferrous metals.

In some embodiments, the pipeline is formed of materials selected from the group consisting of iron, iron alloys, copper, and zinc plating. In some embodiments, the pipeline is formed of materials selected from iron and iron alloys.

Pre-Assessment Step

In the pre-assessment step in the standard ECDA process, historic and current data is collected, ECDA regions are defined, and indirect inspection tools are selected. The types of data to be collected are typically available in construction records, operating and maintenance histories, alignment sheets, corrosion survey records, other aboveground inspection records, and inspection reports from prior integrity evaluations or maintenance actions.

The present invention improves upon this pre-assessment step by analyzing the moisture content and distribution of the soil in which the pipe is buried. Calculations of the moisture content at multiple locations along the length of the pipe is employed first to help choose appropriate indirect inspection methods to obtain the most useful data for further macro-modeling to predict likely areas of corrosion concern. In the pre-assessment step of the present invention, data not previously taken into account by the standard ECDA is collected and employed. This additional data includes one or more of the following: rainfall, evaporation and snowmelt collected from available sources or otherwise experimentally obtained. This data is employed to identify where moisture (necessary for corrosion) exists along the pipe length, and is used to determine the best indirect inspection methods to obtain additional desired data for subsequent modelling of the areas where corrosion is likely based upon electrochemical thermodynamic principles.

While the pre-assessment step according to the present invention may also take into account construction records, operating history, maintenance history and corrosion control records, it is unique in that it takes into account either available data (for example, rainfall data is typically available for given regions where the pipe might be located) or readily determined data (for example, soil may be readily tested for water content) and employs this moisture content data in mathematical models used to identify areas where moisture will lead to corrosion, and help choose appropriate indirect inspection technologies for those areas.

Notably, the pre-assessment step also involves collecting other useful data not specifically directed to moisture content, such as soil chemistry (ion concentrations, pH, resistivity, redox potential), and soil corrosivity, but that data is employed later in the present process, whereas the present focus is on the development of moisture content data used to choose appropriate indirect inspection methods.

Referring now to FIG. 1, the method is employed on a pipe 10 of length Z. Although it may be possible that the pipe 10 only travels through one layer L of soil, FIG. 1 shows a pipe extending through 3 layers, L1, L2, and L3, L1 providing the ground surface 12. In this step, a plurality of locations, z1, z2, z3 . . . zn, along the length of the pipe 10 are chosen for the collection of moisture content data. In some embodiments, the locations are at equally spaced intervals.

This step of the present invention concentrates on estimating the soil moisture content in metric intervals with the following reasoning: (1) soil moisture content is one of the important components directly affecting the risk of pipeline corrosion, i.e., higher soil moisture content results in higher risk of the corrosion; (2) determination of soil moisture in the field and laboratory may be very costly and thus limited data collection cannot cover the entire region (i.e., Mexico in this study); and (3) the distribution of the water with time and pH (determined from available records or direct or indirect inspection methods) can be combined to produce a thermodynamic approach for corrosion feasibility based on the equilibrium conditions of E-pH. In addition, due to the integration of the water and pH distribution in the pre-evaluation process different technologies are considered to deploy at different seasons. To this end, the principle goals of this aspect of the invention are: to estimate soil moisture content at different depths along the length of the pipeline under study; to create long-term quantitative soil moisture content at different depths with the available precipitation, temperature and soil survey information; and to link the spatial distribution of the soil moisture at different depths that related the sites where corrosion will exist.

The moisture content data includes temperature (T), precipitation (P) and Latitude as the coordinate (L) for each desired point z along the length of the pipe. The moisture content data can be obtained from databases of the local meteorological stations or other appropriate sources. For example, in experiments in Mexico, the INEGI (Instituto Nacional de Estadistica y Geografia; National Institute of Statistics and Geography of Mexico) was consulted. In the United States, NOAA—National Oceanic and Atmospheric Administration—may be consulted.

Total precipitation, $P_{total}$, is estimated as the sum of rain and snow melt (SM). The following equations are employed to estimate SM:

$$SM = snostor \times SMF$$

where $SMF = \dfrac{T - T_{snow}}{T_{rain} - T_{snow}} \times meitmax,$ wherein snostor is water acumulación in terms of snow, SMF is the fraction of snostor that will melt in a month, T is mean monthly temperature, $T_{rain}$ is a threshold temperature for rainfall, $T_{snow}$ is a threshold temperature for snowfall and meltmax is the máximum melt rate. Further details about how to estimate SM and SMF are known by those of ordinary skill in the art from McCabe and Wolock, "Future snowpack conditions in the western United States derived from general circulation model climate simulations," Journal of Water Resources Association (35) 1999: p. 1473-1484. Accumulated precipitation is calculated by extracting potential evapotranspiration (PET) from total precipitation ($P_{total}$). PET is estimated using mean monthly temperature using the equation proposed by Hamon, "Estimating potential evapotranspiration," Journal of Hydraulics Division, ASCE, 87 (1961): p. 107-120 as:

$PET_{Hamon} = 13.97 \times d \times D^2 \times W_t$ where:
  PET: mm/month;
  d: number of days in a month;
  D: mean monthly hours of daylight in units of 12 hrs;
  $W_t$: is a saturated water vapor density (g/m$^3$) and can be estimated by:

$$W_t = \frac{4.95 \times e^{0.062 \times T}}{100}$$

where:
  T: temperature in ° C.

Then, starting from first month up to last month we will calculate the initial moisture ($\theta_{start}$):

$$\theta_{start} = \frac{\theta_i^{t-1} \times L_i + \text{influx}}{L_i}$$

where t=1 to N (where N is the total number of time intervals (e.g., day, week, month, year) studied) and i=1 to M (where M is the total number of soil layers).

For the first soil layer: the influx will be equal to PMPE(t) and if initial soil moisture is less than residual soil moisture ($\theta_{start} < \theta_r$) we will have:

$\theta_{start} = \theta_r$ $AET = P_{total} - (\theta_{start} - \theta_1^{r-1}) L_1$ $\text{Deficit} = PET(t) - AET(t)$ otherwise ($\theta_{start} \geq \theta_r$) we will have:

Deficit=0

$AET(t) = PET(t)$

At the next step we will compare the initial moisture ($\theta_{start}$) with the saturated soil moisture ($\theta_z$): If $\theta_{start} \leq \theta_z$: we will not have any outflux from the layer (outflux'=0). If $\theta_{start} > \theta_z$: the outflux from the layer will be calculated by the following equation:

At the next step we will compare the initial moisture ($\theta_{start}$) with the saturated soil moisture ($\theta_z$)): If $\theta_{start} \leq \theta_z$: we will not have any outflux from the layer (outflux'=0); and, if $\theta_{start} > \theta_z$: the outflux from the layer will be calculated by the following equation:

outflux=outflux'+$L_i(\theta_{start} - \theta_i^t)$ where:

outflux'=$L_i(\theta_{start} - \theta_a)$

And $\theta_i^t$ or the soil moisture of the layer i in month t is formulated as:

$$\theta_i^t = \theta_s - \frac{\theta_s - \theta_r}{\alpha} \ln\left[\frac{\alpha K_s}{L(\theta_s - \theta_r)} + \exp\left(\alpha \frac{\theta_s - \theta_{start}}{\theta_s - \theta_r}\right)\right]$$

wherein a is a constant, and is 13 for homogeneous soil layer and 16 for heterogenous soil layer (Bresler et al., "Crop-Evaportanspiration-Guidelines for computing crop water requirement," FAO Irrigation and Drainage Paper 56, Food and Agriculture Organization of the United Nations: Rome (1978); and Russo and Bresler, "Scaling soil hydraulic properties of a heterogeneous field soil," Soil Science of America Journal, Vol. 44, No. 4, pp. 681-684), $K_s$ is constant reaction rate. For the general form of the equation and more details about soil water balance model, reference is made to Kendy et al., "A soil-water-balance approach to quantify groundwater recharge from irrigated cropland in the North China Plain," Hydrological process, 17, pp. 2011-2031 (2003).

For in-situ estimation of soil moisture, soil properties need to be appropriately studied first. Information regarding the composition of the soil through which the pipeline extends is obtained from available sources or on-site surveying. Soil survey information (composition of sand, clay and silt in the soil column) might for example be obtained from the NRCS (Natural Resources Conservation Service) of USDA (US Department of Agriculture). The number of homogeneous layers and their depth, and the soil composition (i.e., percentage of sand, clay and silt) can be estimated for each layer. With identified soil types, the important soil-water properties such as: field capacity ($\theta_{fc}$), wilting-point ($\theta_{wp}$), residual soil moisture ($\theta_r$), saturated soil moisture ($\theta_s$) and saturated hydraulic conductivity ($K_s$) can be determined (given in Table 1).

TABLE 1

Properties of Different Soil Types

| Soil Type | Wilt pt (1500 kPa) ($\theta_{wp}$) % v | Field Cap (33 kPa) ($\theta_{fc}$) % v | Saturation (0 kPa) ($\theta_s$) % v | Residual ($\theta_r$) % v | Saturated Hydraulic conductivity (Ks, cm/day) |
|---|---|---|---|---|---|
| Sand (Sa) | 3.3 | 9.1 | 43.7 | 2 | 504 |
| Loamy sand | 5.5 | 12.5 | 43.7 | 3.5 | 146.64 |
| Sandy loam | 9.5 | 20.7 | 45.3 | 4.1 | 62.16 |
| Loam (L) | 11.7 | 27 | 46.3 | 2.7 | 31.68 |
| Silty loam (SiL) | 13.3 | 33 | 50.1 | 1.5 | 16.32 |

TABLE 1-continued

Properties of Different Soil Types

| Soil Type | Wilt pt (1500 kPa) ($\theta_{wp}$) % v | Field Cap (33 kPa) ($\theta_{fc}$) % v | Saturation (0 kPa) ($\theta_s$) % v | Residual ($\theta_r$) % v | Saturated Hydraulic conductivity (Ks, cm/day) |
|---|---|---|---|---|---|
| Silt (Si) | 6[b] | 30[b] | 46[c] | 3.4[c] | 6[c] |
| Sandy clay | 14.8 | 25.5 | 39.8 | 6.8 | 10.32 |
| Clay loam | 19.7 | 31.8 | 46.4 | 7.5 | 5.52 |
| Silty clay loam | 20.8 | 36.6 | 47.1 | 4 | 3.6 |
| Silty clay | 25 | 38.7 | 47.9 | 5.6 | 2.16 |
| Sandy clay | 23.9 | 33.9 | 43 | 10.9 | 2.88 |
| Clay (C) | 27.2 | 39.6 | 47.5 | 9 | 1.44 |

Figure 2:
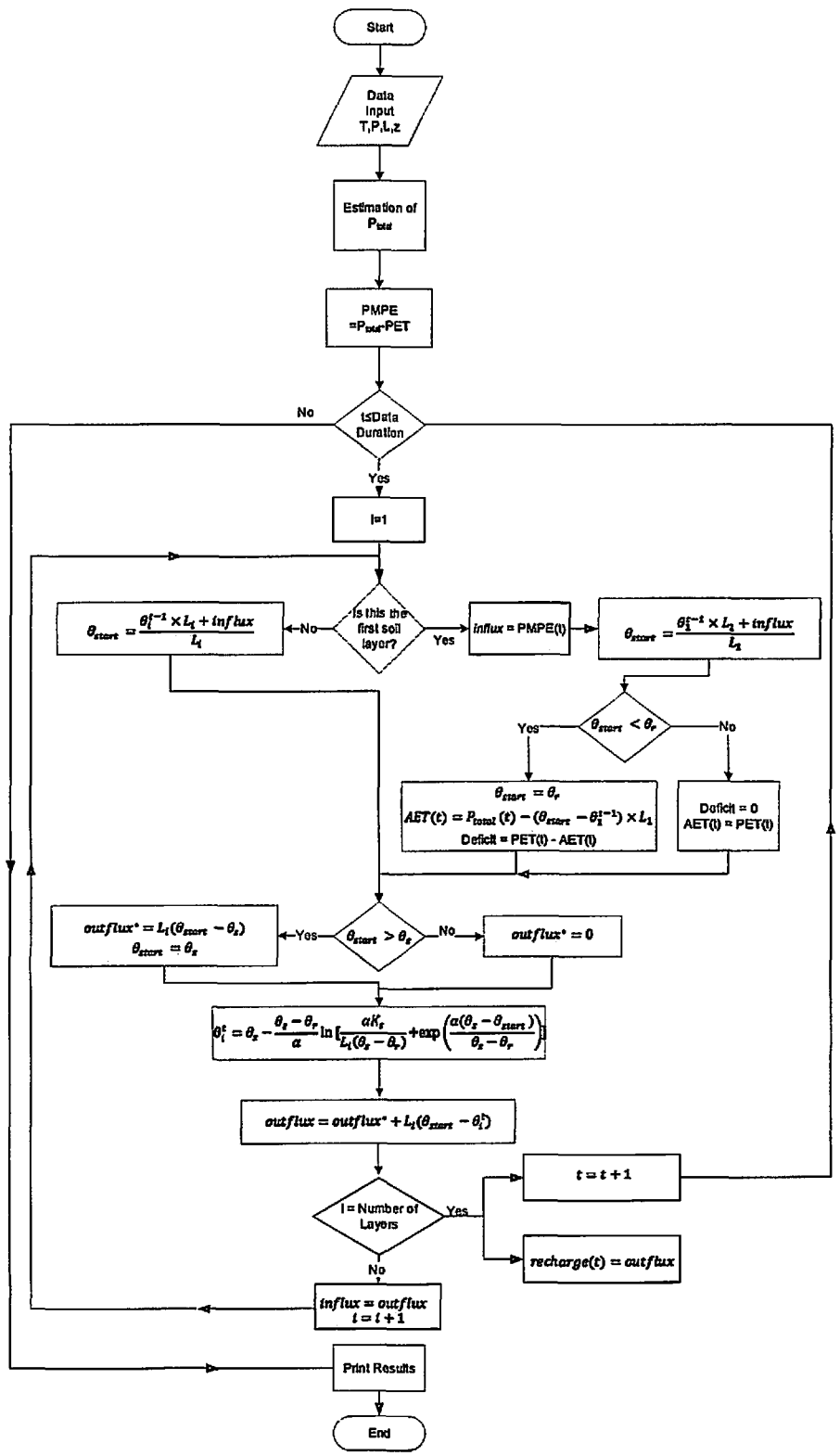
FIG. 2 is a flow chart for making moisture content ($\theta$) calculations for all layers, i, for each of the desired time periods, t, to calculate soil moisture at each layer in all time intervals

As per the flow chart of FIG. 2, the moisture content ($\theta$) calculations are made for all layers, i, for each of the desired time periods, t, to calculate soil moisture at each layer in all time intervals. In some embodiments, the time intervals are month long intervals. These equations will provide time dependent data on the moisture content for each layer at each point z, at each time interval studied. This is beneficial because one can immediately reduce points z necessary for indirect inspections by taking note of those segments of the pipe that, according to calculations, are not exposed to moisture sufficient enough to cause corrosion concerns. In addition to reducing the pipe points z of interest, the moisture content data is used to select appropriate indirect inspection technologies.

In accordance with standard ANSI/NACE ECDA practices a minimum of two indirect inspection tools are to be selected for all locations and regions where ECDA is to be applied along the pipeline and indirect inspection tools are to be selected based on their ability to detect corrosion activity and coating holidays reliably under the specific pipeline conditions to be encountered. A "holiday," in relation to an anticorrosive surface coating, is know in the industry to be a discontinuity in coating, when a part of the surface remains uncoated; a defect such as an area of insufficient coating film thickness; a pinhole within the coating; a crack within the coating; or an improper adhesion or bonding of the coating. With respect to the present invention, the tools are selected based on moisture content and aspects of the soil, which is a novel approach as compared to the ANSI/NACE standard.

The moisture content data is expressed in units of volume of water per volume of soil ($V_{water}/V_{soil}$). With historic time dependent data on moisture content, points z that have been exposed to high levels of water contact can be indentified to help choose appropriate indirect inspection technologies to apply in the indirect assessment step. Additionally, the data can be used to predict/estimate soil conditions of certain points z at the time that the indirect inspection is to take place and these predictions/estimates can be considered to help choose appropriate indirect inspection technologies. The magnitude of Theta ($\theta$) indicates certain water moisture content. If the magnitude of theta is more than zero then the sites is a potential site for corrosive conditions, with a higher magnitude indicating a higher chance for corrosion. Thus, in some embodiments, the chosen indirect inspection technology is based on $\theta$. For negative values of $\theta$, alternating current voltage gradient (ACVG) surveys are used in the indirect assessment step. For positive values of $\theta$, direct current voltage gradient (DCVG) surveys are used in the indirect assessment step. In some embodiments, when $\theta$ is less than or equal to 0.1, alternating current voltage gradient (ACVG) surveys are used in the indirect assessment step. ACVG surveys are a method of measuring the change in leakage current in the soil along and around a pipeline to locate coating holidays and characterize corrosion activity. In some embodiments, when $\theta$ is greater than 0.1, direct current voltage gradient (DCVG) surveys are used in the indirect assessment step. DCVG surveys are a method of measuring the change in electrical voltage gradient in the soil along and around a pipeline to locate coating holidays and characterize corrosion activity.

Indirect Assessment Step

Figure 3:
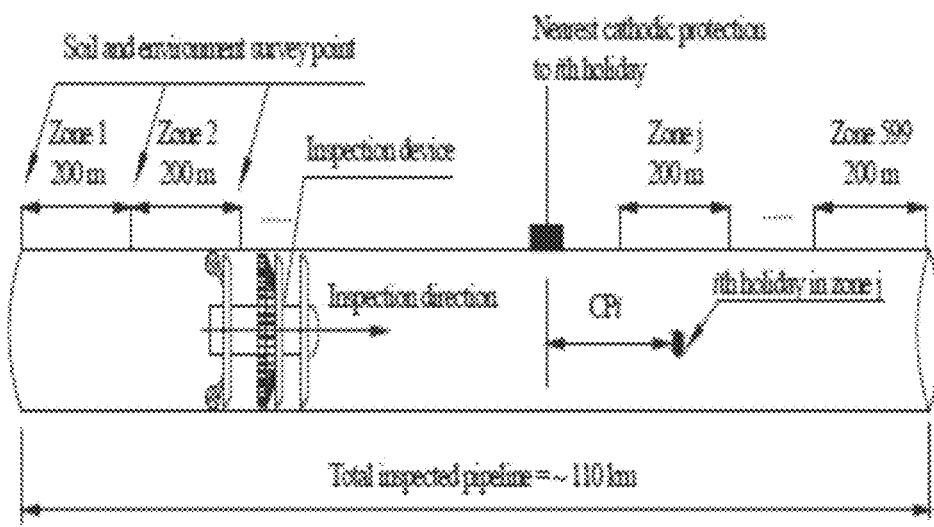

In this indirect assessment step, the present invention focuses on obtaining data regarding the condition of the desired length of pipe and aspects of the surrounding soil. In line inspection is of particular use, as shown in FIG. 3, wherein well known inspection devices—known as "pigs" and carrying out a process known as "pigging"—travel the desired length of the pipe and collect data regarding the corrosion of the pipe and/or other desired data, such as soil conditions or water content and the like. Such in-line inspection can also be supplemented with above-ground indirect inspection methods such as pipe-to-soil potentials, Pearson surveys, close interval surveys, AC current attenuation surveys, direct (DCVG) and alternating current voltage (ACVG) gradient surveys, and cell-to-cell surveys.

This indirect inspection also includes correlating the modeled data regarding moisture content from the pre-assessment step with the data received in the indirect inspections. Cluster analyses are performed to increase the accuracy of the estimation of corrosion rates. In some embodiments, the soil and environmental properties are grouped into similar clusters via clustering models. The filtering of the data by clustering provides reliable means to locate the most corrosive locations along the length of the pipe.

The probability of failure with two different failure conditions can be linked with the environment corrosivity. The probability of failure of specific location can be estimated with the current data or new data obtained from direct technologies, and the corrosivity can be estimated by the interaction of the metal loss with the measured parameters by the indirect inspection surveyor technologies. Cluster analysis classifies the data in different rankings due to the interaction of each measured parameter with the corrosivity environment and indirect technologies measured. The clusters produced soil corrosivity based on the chemistry of the soil and the damage that the environment can cause due to the interaction of the corrosive species on the metallic structure. Decisions for repairing and control can be made with this approach.

In some embodiments, the moisture content and soil properties measured and/or calculated at segments of the pipe are correlated with the growth of defects that are measured by pigging/modeling. Thus, over time, patterns emerge and are employed to increase the accuracy of choosing likely corrosive sites. In some embodiments, clustering involves correlating measured metal losses with one or more of the moisture content, the pH, the ion concentrations, the soil resistivity, redox potential, corrosion potential and the soil type, to find general patterns that help predict where corrosion is likely, not only in the present pipeline but in other pipelines where similar moisture and soil property data is collected.

Reliability Analysis

In some embodiments, a damage evolution model of the corrosion defects is developed based on the fielding data obtained from pigging technology. The results of the analysis provide data regarding the performance of each segment of the pipeline over time. Therefore, the necessary further inspection, repair, and/or maintenance can be scheduled.

The desired length of pipeline is analyzed by pigging technology to identify defects. The pigging technology is used to detect the pipeline wall thickness loss (i.e. corrosion defects) at different times. Preferably, a pigging later in time will inspect the same defects that have been detected in a previous pigging and matched defects are compared Matched defects refer to the defects in the same location. The depth of the matched defects can be different at different inspection time as the corrosion depth changes with time. In some embodiments, two defects are considered to be matched if they are within ±2 km of each other. In other embodiments, the defects are considered to be matched if they are within ±5 km of each other. In instances where different pigging technology has been applied at different times, the defects that have been detected by one technology will not necessarily be detected by the other. In these situations, where desired data is scarce, to be conservative for the reliability analysis, it is assumed that all the defects detected by the pigging technologies are the true defects and the inspection error is ignored in the analysis due to a lack of relevant information. Furthermore, the depth detected can be considered as the maximum depth of the defect.

Damage Evolution Model

The length of a studied pipeline is typically on the order of tens, if not hundreds or more, kilometers, and thus the growth of corrosion damage varies along the length in light of the different environmental conditions to which the pipeline is exposed at different locations. In some embodiments, the length of pipe under study is divided into n continuous segments. For each segment, it is assumed that the growth of the corrosion damage can be described by the same damage evolution model. How to divide the segment will be discussed later below.

To describe the damage (corrosion defect) growth over time, the damage state at a time instant and damage rate (corrosion rate) can be used, particularly when data regarding particular defects are such that two damage states for the same defects are known and growth rates can then be calculated. In some embodiments, to evaluate the corrosion rate, two damage states for the same defect are needed, so the change over time can be assessed. In embodiments where such data is not available, an alternative modeling is needed.

In this modeling, the depth of a corrosion detect in the ith segment of pipeline is modeled for through a power-law function of time as shown below:

$$d_i(t) = \theta_{1i}(t-t_{0i})^{\theta_{2i}} + \sigma_i \varepsilon_i \quad i=1, 2, \ldots, n \quad (1)$$

where $d_i(t)$=defect depth at a time instant t, $\theta_{1i}$ and $\theta_{2i}$=unknown model parameters, $t_{0i}$=initiation time of defect, $\varepsilon_i$=random variable with zero mean and unit variance, and $\sigma_i$=standard deviation of the model error. Note that $t_{0i}$ is unknown as well in this study. To evaluate $t_{0i}$, we can assume for each segment, the number of defects that occurs follows the same homogeneous Poisson process characterized by a rate parameter $\lambda_i$.

Additionally, it is reasonable to assume that in the same segment, the defect with largest depth occurs first. Then, the defects in the same segment (say, there are $m_i$ defects in the ith segment) can be sorted based on their depth values $(d_{i,1} \geq d_{i,2} \geq \ldots \geq d_{i,mi})$ and thus the initiation time, $d_{i,j}$ (j=1, 2, ..., $m_i$) follows Gama distribution with shape parameter j and a scale parameter $1/\lambda_i$. In other word, $t_{0i}$ is characterized by a Poisson process with a unknown rate parameter $\lambda_i$. Let $\Theta_i = \{\theta_{1i}, \theta_{2i}, \lambda_i\}$ and thus $\theta_i$ is the unknown parameter vector for Eq. (1). The inspection data obtained from the inspections will be used to assess $\Theta_i$ through a method called Bayesian model updating.

Bayesian statistics (Box and Tiao 1992) enables us to use the field data to update the joint probability density function (PDF) $p(\Theta_i)$ of the unknown parameters, $\Theta_i$, used in the damage evolution model. If $X_i$ denotes the vector of data used to update the model parameters, the posterior PDF of $\Theta_i$, $p'(\Theta_i)$, can be written as $$p'(\Theta_i) = \kappa L(X_i|\Theta_i) p(\Theta_i) \quad (2)$$

where $\kappa = [\int L(X_i|\Theta_i) p(\Theta_i) d\Theta_i]^{-1}$, and $L(X_i|\Theta_i)$=likelihood function. As the model error in Eq. (1) follows a normal distribution, the likelihood function can be written as $$L(X_i|\Theta_i) = \frac{1}{\prod_j (2\pi \cdot \sigma_{i,j})} \exp\left\{\sum_j \frac{(\tilde{d}_{i,j} - d_{i,j})^2}{-2\sigma_{i,j}^2}\right\} \quad (3)$$

where $d_{i,j}$=the depth of the jth defect in the ith segment predicted using Eq. (1) and $\tilde{d}_{i,j}$=depth measured by the inspection.

However, calculating the normalizing factor $\kappa$ can be challenging, especially when the dimension of x is high. To effectively compute the posterior statistics, one can use a sampling-based technique like the Markov Chain Monte Carlo (MCMC) simulations (Gilks et al. 1996). MCMC generates a sequence of random variables called Markov chain such that the current value or state of the sequence depends only on the previous value. Given certain conditions, the chain will forget its initial state and converge to a stationary distribution. For the convergence criteria, the Geweke method (Geweke 19992) is used in this paper, which provides unbiased estimates of the posterior statistics.

Reliability Analysis

The goal of reliability analysis is to evaluate the probability of failure of the pipeline system. Probability of failure (or fragility) is defined as the conditional probability of attaining or exceeding prescribed limit states given set of boundary variables. Following the conventional notation in structural reliability (Dilevsen and Madsen 1996), probability of failure (fragility) of the kth failure mode at moment t can be expressed by:

$$P_f^k(t) = P\{g_k \leq 0 | t\} \quad (4)$$

Where P is probability, $[g_k \leq 0]$=failure event and $g_k$=limit state function for the kth failure mode. Two limit states corresponding to two failure modes are considered: small leak and large leak. Small leak indicates the defect penetrates the pipe wall, and the limit state function can be expressed as $$g_1 = d_w - d(t) \tag{5}$$

where $d_w$=pipeline wall thickness, and d(t)=the maximum depth of a corrosion defect. For the large leak, the limit state function is shown as $$g_2 = C_p(t) - D_p \tag{6}$$

where $C_p$ and $D_p$=pressure resistance and pressure demand, respectively.

Figure 4:
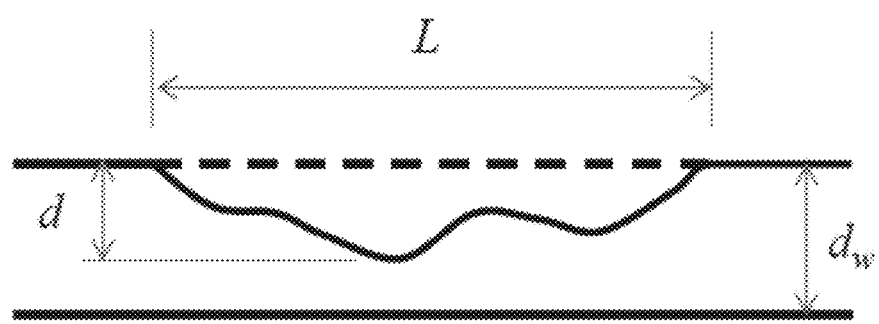
FIG. 4 is a schematic of a defect in a pipe wall used to help describe variables of equations provided herein.

The pressure resistance will be evaluated using $C_p = e_m \cdot P_u$ where $e_m$ is the model error and $P_u$ (Pressure of pipeline) is evaluated based on ASME B31 G Code as following:

$$p_u(t) = 1.1\sigma_{min,y} \cdot \frac{2d_w}{D_o} \cdot \frac{1 - \frac{2}{3}\frac{d(t)}{d_w}}{1 - \frac{2}{3}\frac{d(t)}{d_w}M^{-1}} \tag{7}$$

where $\sigma_{min,y}$=specified minimum yielding stress, $D_o$=outer diameter of the pipeline, M=Folias factor and is determined by $$M = \begin{cases} 1 + 0.6275\frac{L^2}{D_o d_w} - 0.003375\frac{L^4}{D_o^2 d_w^2} & \text{for } \frac{L^2}{D_o d_w} \leq 50 \\ 3.3 + 0.032\frac{L^2}{D_o d_w} & \text{for } \frac{L^2}{D_o d_w} > 50 \end{cases} \tag{8}$$

where L=defect length as shown in FIG. 4.

For each defect, the fragility of the two failure modes can be calculated given a time instant. If let $t_1$ to the last inspection time for a defect, and let $t_2$ be an time instant after $t_1$, the defect depth predicted by Eq. (1) at these two time instants are $$d_i(t_1) = \theta_{1i}(t_1 - t_{0i})^{\theta_{2i}} + \sigma_i \varepsilon_i \tag{9}$$

$$d_i(t_2) = \theta_{1i}(t_2 - t_{0i})^{\theta_{2i}} + \sigma_i \varepsilon_i \tag{10}$$

With Eqs. (9) and (10), we can write $$d_i(t_2) = d_i(t_1) + \theta_{1i}(t_2 - t_{0i})^{\theta_{2i}} - \theta_{1i}(t_1 - t_{0i})^{\theta_{2i}} + \sqrt{2}\sigma_i \varepsilon_i \tag{11}$$

In Eq. (11), as $t_1$ refers to the last inspection time, $d_i(t_1)$ is the depth obtained from the inspection. Thus, the field data is used to predict the future corrosion growth.

To consider the reliability of the pipeline system, the fragility of pipeline per km is computed. In other word, the entire pipeline system is divided into $n_f$ sub-system, and each sub-system has 1 km length. Then the fragility of each sub-system is computed using the fragility associated with the defects that are within the sub-system. If the sub-system is considered as a series system consistent with a set of defects, then the failure on one defect indicates the failure of the sub-system. Thus, the fragility of the ith sub-system with $m_i$ defects can be computed using $$P_{f,i}^k(t) = 1 - \prod_{j=1}^{m_i}[1 - P_{f,ij}^k(t)] \tag{12}$$

Results and Discussion

Figure 5:
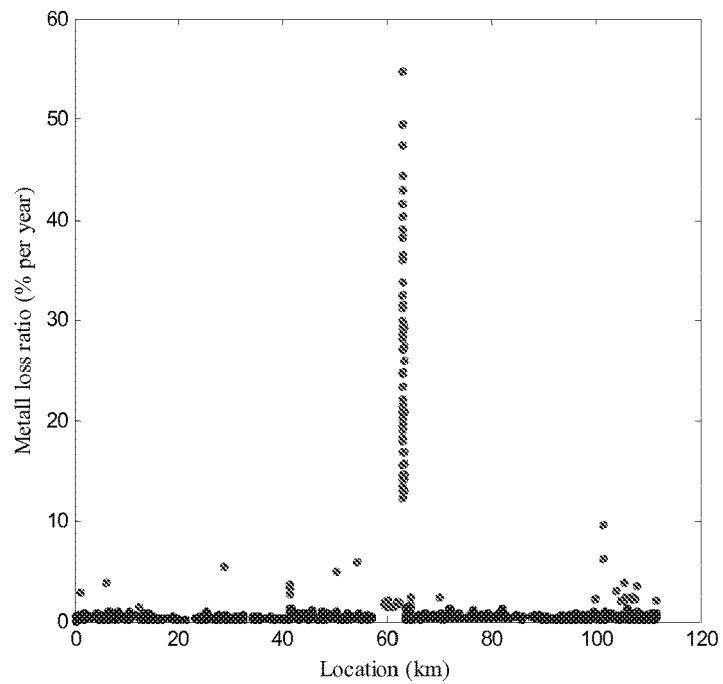
FIG. 5 shows an exemplary graph of the average rate of the metal loss of all inspected defects along a 112 km length of pipeline analyzed in an experimental study
Figure 6:
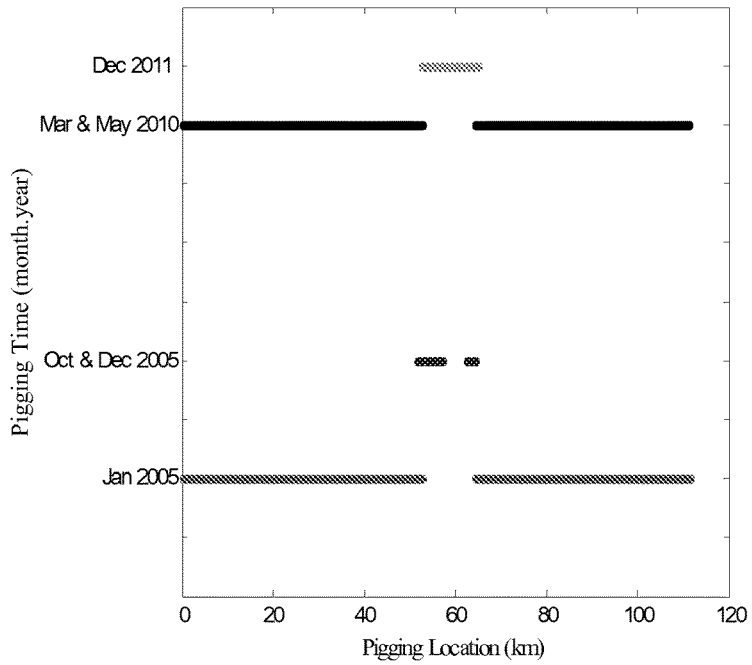
FIG. 6 shows the length of a 112 km pipeline assessed by pigging technologies at various times.

As indicated previously, the pipeline is divided into a desired number of segments and it is assumed that defects within each segment follow a similar trend of corrosion defect growth. First, an average rate of metal loss is used to see how the growth of defect varies with the length. The average rate of metal loss is calculated by using the metal loss percentage of a defect divided by the time interval between the inspection time and the installation time. FIG. 5 shows an exemplary graph of the average rate of the metal loss of all inspected defects along a 112 km length of pipeline analyzed in an experimental study. Table 2 shows major characteristics of the studied pipeline. The pigging technology has been applied to detect the pipeline wall thickness loss (i.e. corrosion defects) at six different times. Table 3 shows the number of defects found in each pigging. FIG. 6 further indicates the pigging location and time. Table 4 shows matched defects at different tolerances. Even though the pipeline had been inspected six times, each time the application areas were not the same. Overall, there were overlapping areas between January 2005 Pigging and March & May 2010 Pigging, and there were overlapping areas between October & December 2005 Pigging and December 2011 Pigging.

TABLE 2

Pipeline characteristics

| | |
|---|---|
| Length | 110 km |
| Diameter | 457.20 mm |
| Wall thickness | 6.41 mm |
| Steel type | API 5L X52 |
| Minimal yielding stress | 52 ksi |

TABLE 3

Summary of number of defects found in pigging

| Pigging date | Total number of defects |
|---|---|
| January 2005 | 795 |
| October 2005 | 110 |
| December 2005 | 44 |
| March 2010 | 1614 |
| May 2010 | 332 |
| December 2011 | 66 |

TABLE 4

Number of matched defects

| | Tolerance for location difference | |
|---|---|---|
| Data used for matching | ±5 km | ±2 km |
| January 2005 vs March & May 2010 | 25 | 11 |
| October & December 2005 vs December 2011 | 0 | 0 |

In FIG. 5, the mass of data points (dots) at the base are the defects on the older pipeline that were installed on 1969, and the more distinct data points seen above this general base line are the defects on the newer pipeline sections installed between 2001 to 2005. As seen in FIG. 5, the average rates of the metal loss of those defects on the newer pipeline are much higher than the ones on the older pipeline. This indicates that the defect growth should be modeled separately for those two groups of defects. Furthermore, the defects within 58 km to 63 km have extremely high rates.

Within only about 0.8 years that is the time interval between the installation of the pipeline to the inspection, up to 42% of metal loss has been found. Thus, the defect values within 58 km to 63 km need to be further verified before those data are used for the modeling.

In this study the damage evolution is modeled using Eq. (1) using the defect values on the older pipeline, which are the defects shown as blue dots in FIG. 5. In other word, the unknown parameter $\Theta_i$, will be assessed using the depths of the defects within each segment of the pipeline installed on 1969. The segment length cannot be too short; otherwise, not enough number of defects within that segment can be used to assess the unknown parameters, which can cause a large variability in $\Theta_i$. The segment length cannot be too long; otherwise, the variability of the damage evolution characteristics along the pipeline length cannot be captured. With that in mind, the 112 km of the pipeline is grouped as shown in FIG. 7. Table 5 gives the statistics of $\Theta_i$ for all the segments.

Figure 9:
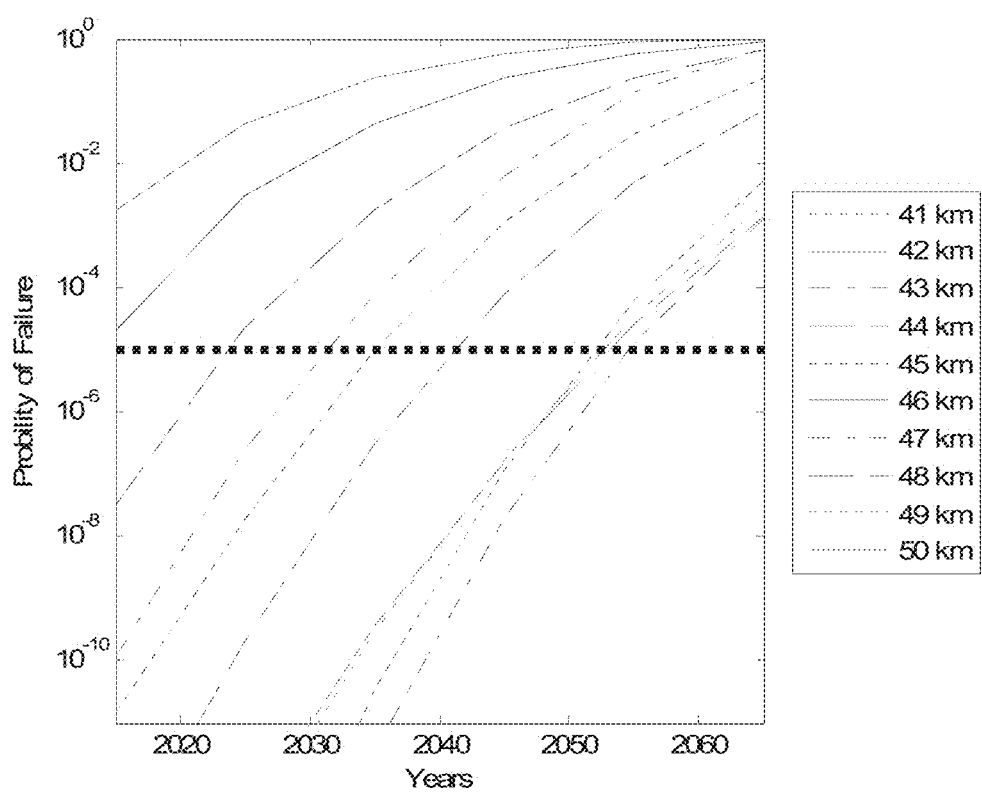
FIG. 9 shows the fragilities for small leak failure modes for the forty-first through fiftieth kilometer segments of a 112 km length of pipeline under study herein.
Figure 10:
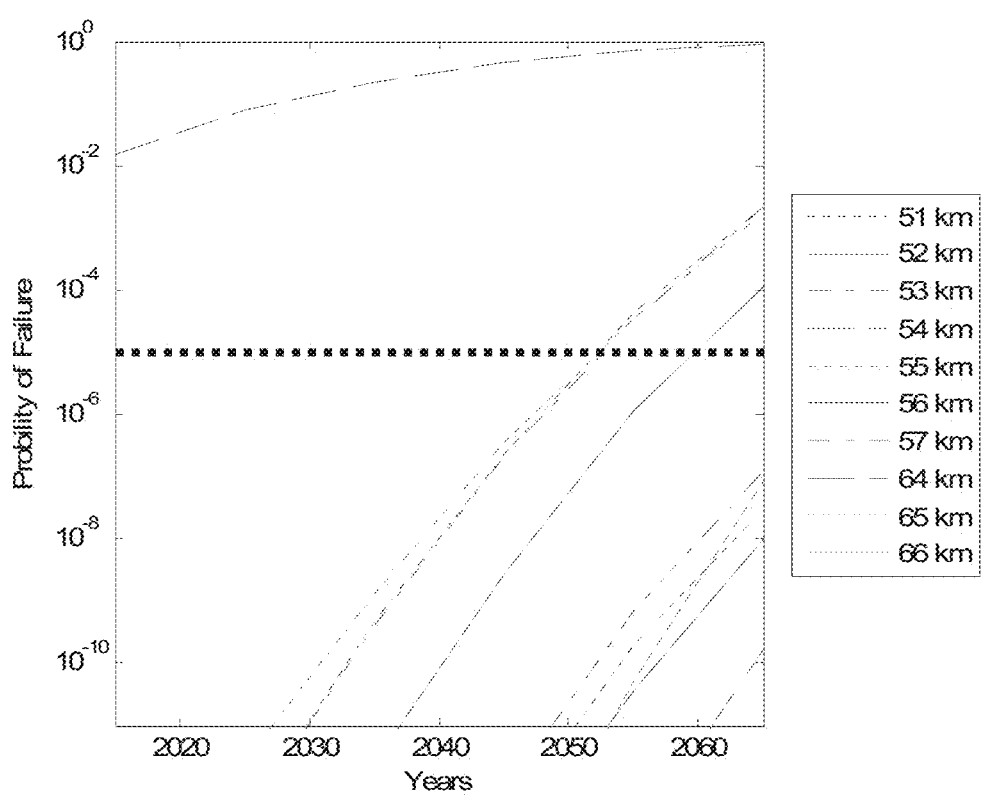
FIG. 10 shows the fragilities for small leak failure modes for the fifty-first through sixtieth kilometer segments of a 112 km length of pipeline under study herein.

With the parameters in the damage evolution model are evaluated, the fragility of pipeline per km can be assessed using reliability analysis. Two failure mode: small leak and large leak are assessed separately. Note that, to assess fragility of the second failure mode (the corresponding limit state is shown in Eq. (6)), the defect length L and operation pressure $D_p$ are needed. Since the inspection only detect the defect depth and the operation pressure are not constant, the fragility will be assess given certain values of L and $D_p$. Other random variables that are considered in the reliability analysis are shown in Table 6. The model error $e_m$ in the capacity model of pressure resistant is assumed to be 1.0.

study, the target probability of failure is set to be $10^{-5}$, which is suggested by Ahammed and Melchers (1996) for ASME location class category 2 (fringe areas around towns and cities, industrial areas, ranch/country estates). The target probability of failure is also indicted in the figures using blacked dotted horizontal line. The curve beyond this horizontal line indicates the failure of the performance requirement. The starting point in x-axis is Year 2015 and three sub-systems are found not to meet the performance requirement already at beginning. They are sub-systems 42 km (shown in FIG. 9), 46 km (shown in FIG. 9), and 64 km (shown in FIG. 10). Sub-systems 48 (shown in FIG. 9) and 7 (shown in FIG. 8) fail to meet the requirement at around Year 2020 and 2030. Note that for the curves of the sub-systems that are indicated in the legend but are not shown in the figure, it indicates that the fragilities of those sub-segments are smaller than $10^{-11}$ and thus those sub-systems are not critical.

To assess fragilities of large leak failure mode, different defect length values are used by considering three defect length and depth ratios, L/d(t), to be 2, 10, and 20, respectively. Note that when a defect length and depth ratio is assumed, this ratio is applied to all defects, which is a very rough assumption. However, such assumption has to be made since no defect length information is available.

Figure 11:
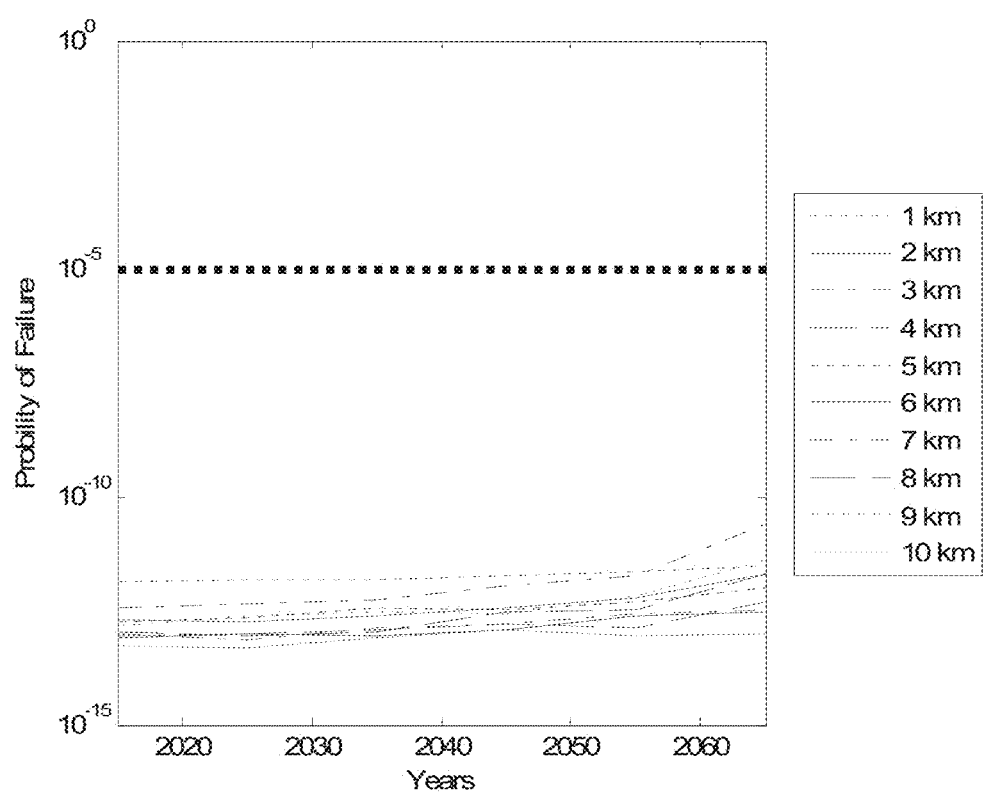
FIG. 11 shows the fragilities for large leak failure modes with L/d(t)=2 for the first through tenth kilometer segments of a 112 km length of pipeline under study herein.
Figure 12:
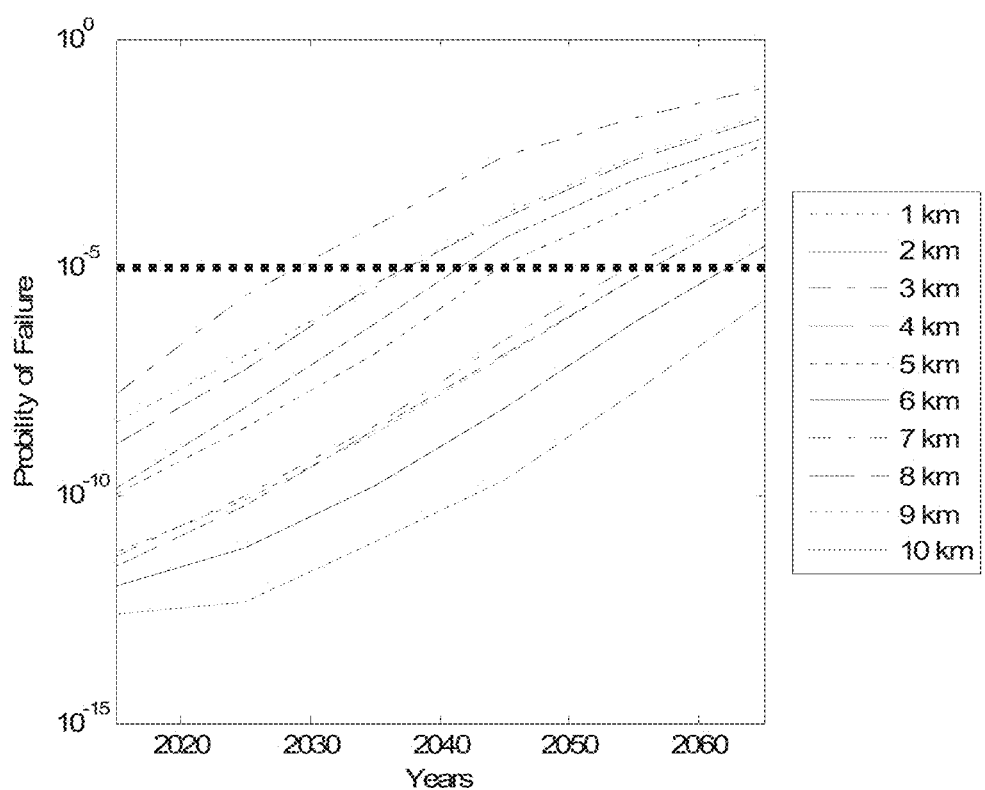
FIG. 12 shows the fragilities for large leak failure modes with L/d(t)=10 for the first through tenth kilometer segments of a 112 km length of pipeline under study herein.

FIG. 11 shows the fragilities for large leak failure mode with L/d(t)=2 for the first through tenth kilometer segments, i.e. from 0 to 10 kilometers. Similar graphs were created for kilometers 11 through 112. FIG. 12 shows the fragilities of large leak failure mode with L/d(t)=10 for the first through tenth kilometer segments. Similar graphs were created for

TABLE 5

Posterior statistics of the parameters in the damage evolution model

| Segment number | $\theta_1$ Mean | $\theta_1$ Std. | $\theta_2$ Mean | $\theta_2$ Std. | $\Lambda$ Mean | $\Lambda$ Std. | $\rho_{\theta1,\theta2}$ | $\rho_{\theta1,\lambda}$ | $\sigma$ |
|---|---|---|---|---|---|---|---|---|---|
| 1 | −2.719 | 0.277 | 0.908 | 0.080 | 1.12E−04 | 0.025 | −0.972 | 0.020 | 0.275 |
| 2 | −2.665 | 0.308 | 0.895 | 0.091 | 1.13E−04 | 0.025 | −0.973 | 0.014 | 0.266 |
| 3 | −2.606 | 0.547 | 0.778 | 0.155 | 1.38E−05 | 0.003 | −0.992 | 0.012 | 0.198 |
| 4 | −2.842 | 0.323 | 0.893 | 0.090 | 5.96E−05 | 0.013 | −0.987 | 0.019 | 0.242 |
| 5 | −2.842 | 0.323 | 0.893 | 0.090 | 4.33E−05 | 0.010 | −0.987 | 0.019 | 0.177 |
| 6 | −2.360 | 0.296 | 0.905 | 0.083 | 5.33E−05 | 0.012 | −0.986 | 0.025 | 0.340 |
| 7 | −2.577 | 0.288 | 0.912 | 0.081 | 3.12E−05 | 0.007 | −0.982 | 0.012 | 0.362 |
| 8 | −2.077 | 0.638 | 0.670 | 0.183 | 3.02E−05 | 0.007 | −0.994 | 0.008 | 0.288 |
| 9 | −2.714 | 0.297 | 0.900 | 0.090 | 1.07E−04 | 0.024 | −0.986 | 0.017 | 0.232 |
| 10 | −2.605 | 0.372 | 0.865 | 0.109 | 1.27E−04 | 0.028 | −0.992 | 0.015 | 0.207 |
| 11 | −1.724 | 0.823 | 0.597 | 0.247 | 4.05E−05 | 0.009 | −0.994 | 0.009 | 0.253 |
| 12 | −2.263 | 0.501 | 0.679 | 0.143 | 2.53E−04 | 0.057 | −0.996 | 0.009 | 0.199 |
| 13 | −2.606 | 0.379 | 0.838 | 0.106 | 4.31E−04 | 0.096 | −0.997 | 0.018 | 0.196 |
| 14 | −2.692 | 0.336 | 0.865 | 0.094 | 4.97E−04 | 0.111 | −0.996 | 0.017 | 0.201 |
| 15 | −2.663 | 0.136 | 0.951 | 0.040 | 4.28E−05 | 0.010 | −0.911 | 0.010 | 0.395 |

TABLE 6

Probabilistic characteristics of basic random variables

| Parameter | Distribution | Mean | COV |
|---|---|---|---|
| Outer diameter of pipe, $D_o$ | Deterministic | 457.20 mm | 0% |
| Wall thickness, $d_w$ | Normal | 6.40 mm | 5% |
| Specified minimum yielding stress, $\sigma_{min,y}$ | Normal | 358.53 MPa | 3.4% |
| Operation pressure, $D_p$ | Normal | 800 MPa | 5% |

Figure 8:
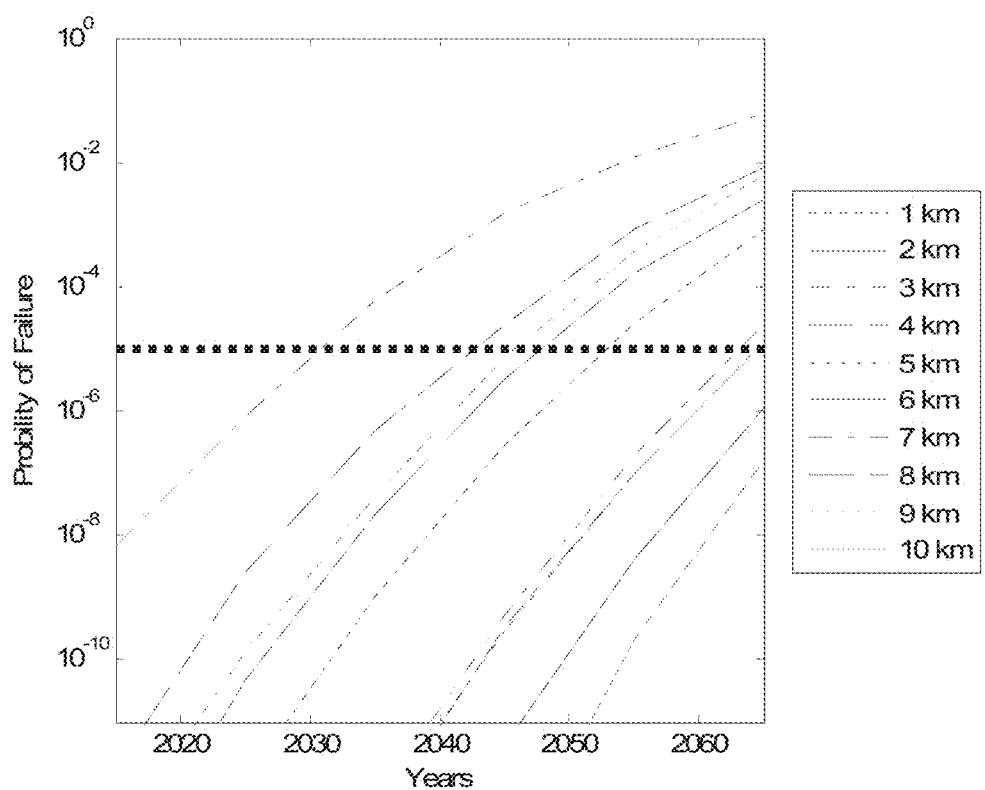
FIG. 8 shows the fragilities for small leak failure modes for the first through tenth kilometer segments of a 112 km length of pipeline under study herein.
Figure 13:
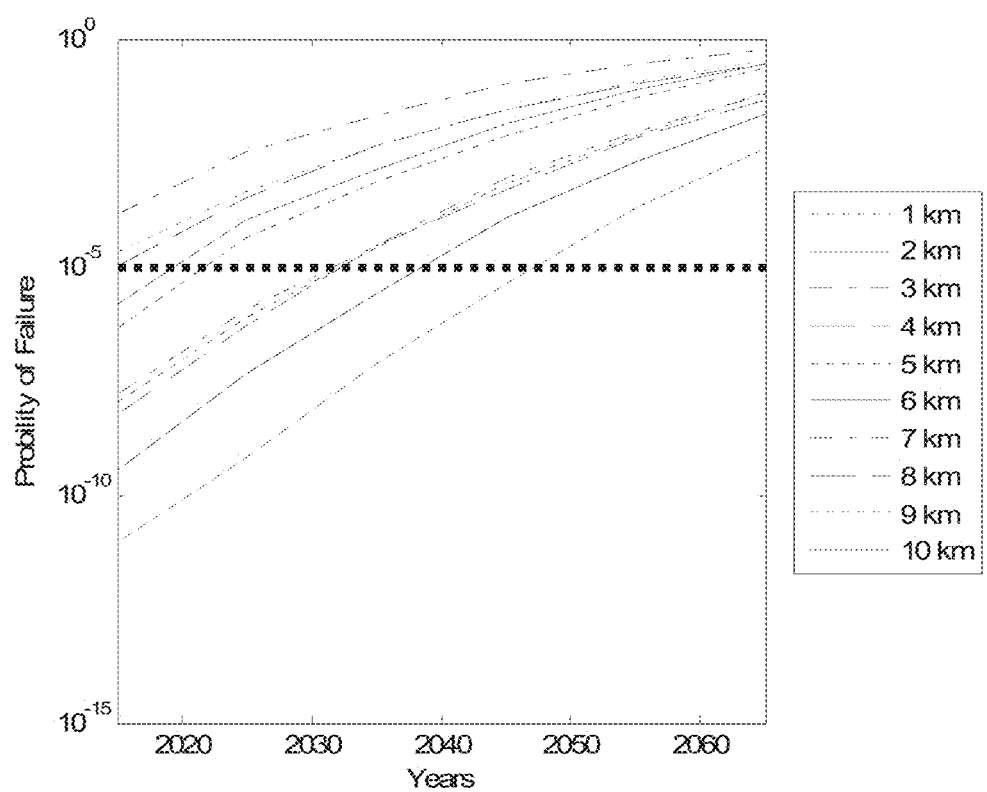
FIG. 13 shows the fragilities for large leak failure modes with L/d(t)=20 for the first through tenth kilometer segments of a 112 km length of pipeline under study herein.

FIG. 8 shows the fragilities for small leak failure modes for the first through tenth kilometer segments, i.e. from 0 to 10 kilometers. Similar graphs were created for kilometers 11 through 112. As expected, they all increase with time. In this kilometers 11 through 112. FIG. 13 shows the fragilities of large leak failure mode with L/d(t)=20 for the first through tenth kilometer segments. Similar graphs were created for kilometers 11 through 112.

For the large leak failure mode, defect length and depth ratio plays a significant role. For example, in FIG. 11 where L/d(t) is assumed to be 2, the fragilities of all the sub-systems are below the black dotted lines, indicating that their performance meet the requirement even at Year 2065. However, if L/d(t) is assumed to be 10 as shown in FIG. 12, the sub-systems start to fail to meet the requirement at around Year 2030. If L/d(t) is assumed to be 20 as shown in FIG. 13, fragilities of sub-systems 7 km to 9 km have already exceed the target probability of failure at Year 2015. This result points out that it is critical to obtain the defect lengths during inspection for accurately evaluating pipeline performance.

In this study, when $L/d(t)=2$, no sub-system will exceed the target fragility for the large leak failure mode until 2035. The sub-systems that exceed the target probability of failure at Year 2015 and Year 2025 are summarized in Table 7. Those sub-systems should be considered as critical components in the pipeline system and should be put first priority in terms of maintenance, repair, and/or replacement.

TABLE 7

Sub-systems (km) that exceed target probability of failure

| Failure modes | Exceed @ Year 2015 | Exceed @ Year 2025 |
|---|---|---|
| Small leak | 42, 46, 64 | 48 |
| Large leak with $L/d(t) = 2$ | None | None |
| Large leak with $L/d(t) = 10$ | 42, 46, 51, 64 | 43, 48, 72, 106 |
| Large leak with $L/d(t) = 20$ | 7, 8, 9, 11, 26, 42, 43, 45, 46, 48, 49, 51, 53, 55, 64, 72, 73, 77, 100, 106 | 2, 5, 14, 15, 44, 50, 65, 68, 71, 76, 80, 102, 103, 107, 108, 109, 111 |

Direct Assessment Step

Direct assessments can be made to supplement the indirect assessment and pre-assessment modeling. Data obtained through indirect assessment and direct assessment may be employed to further improve the modeling such that, over time, very accurate models are generated to identify the most problematic locations along the length of the pipe.

Direct examination may include excavations, analysis of coding damage and corrosion depth, analysis of corrosion causes, and the like.

Post-Assessment Step

The post-assessment step involves analyzing the data to determine the effectiveness of the models and/or the indirect or direct inspection techniques employed.

Thus, the present invention provides an assessment method very similar to the known External Corrosion Direct Assessment (ECDA) process, but advantageously employs a deterministic formulation based on modeling likely corrosion based on various variables such as rainfall and soil conditions, predicting likely areas of corrosion based on electrochemical thermodynamic principles. The measured parameters can be analyzed against measured metal loss whether from indirect inspection or whether direct inspection methods. Cluster analysis provides additional benefits.

External corrosion direct assessment (ECDA) for buried pipelines includes four steps in the Standard Practice for ECDA as a recommended methodology. The first step in the methodology is the preevaluation, the second is the indirect inspection, the third includes the direct assessment and the fourth step is the post assessment. For the first step we propose the integration of macro-parameters, such as rainfall, water accumulation, chemistry of the soil, and soil corrosivity that will localized the zones or areas that are most likely to have active corrosion based on electrochemical thermodynamics principles. These parameters are associated with indirect measurement influencing corrosion (as time-dependent threats that form an electrochemical system) for underground pipelines. This method aims to provide an assessment of the corrosivity of the soil about a buried pipeline based on the interaction of the parameters that cause corrosion and the metallic structure of the pipeline by considering the interaction of at least two parameters. The macro-modeling was included and was based on the parameters affecting the soil properties in different regions during different seasons due to the climate, rainfall, soil properties and environmental parameters. The noise of the field data obtained from indirect surveys and direct assessments can be reduced based on a statistical approach, and the soil and environmental properties are then grouped into similar clusters via clustering models in order to increase accuracy of the estimation of the corrosion rate in an underground pipeline. The statistical analysis helps to develop the pre-evaluation, the filtering of the indirect inspection data, the analysis of the direct assessment and post assessment step for the ECDA process. The clustering analysis can lead to the identification of high corrosion areas and classify different indications that are quantified by indirect measurements. The probability of failure is used to link the cluster classification to identity the zones where the failure is most likely to occur not only due to the interaction with the environment but also due to operation conditions of the metallic structure or pipeline. We developed a method to identify the corrosion potential areas that exist in the external surface of buried pipelines when the coating does not exist due to a failure. The coating failure indications are identified by direct inspections or indirect inspections. The indirect inspections also characterize the environment that surrounds such defect. The filtering and decision of the corrosivity due to the exposed environment and the interaction of the corrosion precursors has been developed by statistical tools. Indication repairing method and control is established by the combination of the following methods and techniques: corrosivity of the soil that indicates the sites due to the aggressiveness of the environment, failure probability that indicates the failure probability in that site, and indirect inspection that indicates the likelihood of corrosion. The selection of the excavation/dig site include the three different methods, clustering, failure probability and alignment with indirect inspection data.

In light of the foregoing, it should be appreciated that the present invention significantly advances the art by providing a method for evaluating external corrosion damage in a buried pipeline. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for assessing damage to the exterior of a buried pipeline comprising the steps of:
    calculating a moisture content of soil through which the pipeline extends at a plurality of locations along a length of the pipeline;
    conducting holidays indirect inspection of the plurality of locations through the application of alternating current voltage gradient surveys and direct current voltage gradient surveys, wherein at locations where the moisture content is less than or equal to a first value, an alternating current voltage gradient (ACVG) survey is applied and, at locations where the moisture content is greater than the first value, a direct current voltage gradient (DCVG) survey is applied.
2. The method of claim 1, wherein the moisture content is calculated according to:

$$\theta_i^t = \theta_s - \frac{\theta_s - \theta_r}{\alpha} \ln\left[\frac{\alpha K_s}{L(\theta_s - \theta_r)} + \exp\left(\alpha \frac{\theta_s - \theta_{start}}{\theta_s - \theta_r}\right)\right], \text{ and } \theta_{start} = \frac{\theta_i^{t-1} \times L_i + influx}{L_i},$$

wherein t=1 to N, wherein N is a total number of time intervals, i=1 to M, where M is a total number of soil layers, $\theta_s$ is saturated soil moisture, $\theta_r$ is residual soil moisture, $\alpha$ is a constant, $K_s$ is saturated hydraulic conductivity, $L_i$ is layer thickness and $\theta_{start}$ is initial moisture.

3. The method of claim 2, wherein, when $\theta_i^t$ is less than or equal to 0.1, the ACVG survey is applied, and, if $\theta_i^t$ is greater than 0.1, the DCVG survey is applied.

4. The method of claim 1, further comprising the step of conducting soil indirect inspection of the plurality of locations to obtain soil properties selected from the group consisting of moisture content, pH, ion concentrations, soil resistivity, redox potential, corrosion potential and soil type, wherein ion concentrations are selected from concentrations of $HCO^{3-}$, $Cl^-$, $SO_4^{2+}$ and $CO_3^{2-}$.

5. The method of claim 1, further comprising the steps of: conducting pigging inspection of the plurality of locations and thereby identifying defects within a wall of the pipeline and providing data regarding the metal loss at each defect, calculating metal loss rates from said data regarding metal loss at each defect.

6. The method of claim 5, further comprising the step of clustering the data regarding metal loss rates with the moisture content calculated in said step of calculating the moisture content and with the soil properties of said step of conducting soil indirect inspection.

\* \* \* \* \*